United States Patent [19]
Wang et al.

[11] Patent Number: 6,007,984
[45] Date of Patent: Dec. 28, 1999

[54] DETECTION OF DNA/RNA BY FLUORESCENCE POLARIZATION

[75] Inventors: Chao-huei Jeffrey Wang, Gurnee; Harryl Ammons, Waukegan; Michael E. Jolley, Round Lake, all of Ill.

[73] Assignee: Zeneca Limited, London, United Kingdom

[21] Appl. No.: 08/247,629

[22] Filed: May 23, 1994

Related U.S. Application Data

[63] Continuation of application No. 07/683,923, Apr. 11, 1991, abandoned, which is a continuation-in-part of application No. 07/430,844, Nov. 1, 1989, abandoned.

[51] Int. Cl.$^6$ ............................ C12Q 1/68; C07H 21/00; C12P 19/34
[52] U.S. Cl. ............................ 435/6; 435/91.2; 536/24.3
[58] Field of Search ...................... 435/6, 91.2; 536/24.3

[56] References Cited

U.S. PATENT DOCUMENTS

| | | | |
|---|---|---|---|
| 4,420,568 | 12/1983 | Wang et al. | 436/536 |
| 4,683,202 | 7/1987 | Mullis | 435/91 |
| 4,687,732 | 8/1987 | Ward et al. | 435/6 |
| 4,820,630 | 4/1989 | Zaub | 435/5 |
| 4,835,263 | 5/1989 | Nguyen et al. | 536/27 |

FOREIGN PATENT DOCUMENTS 0 382 433   8/1990   European Pat. Off. .

OTHER PUBLICATIONS

Byrne et al., "Detection of HIV–1 RNA sequences by in vitro DNA Amplification", Nucleic Acids Research, vol. 16, No. 9, p. 4165 (1988).

Arnold, LJ et al., "Assay formats involving acridinium–ester–labeled DNA probes." Clin. Chem. 35:1588–1594 (1989) Abstract.

Kwoh, D. and Kwoh, T. "Target amplification systems in nucleic acid–based diagnostic approaches", *American Biot. Lab.*, 18 pp. 14–25 (1990).

Gingeras, T.R. et al., "Unique features of the self–sustained sequence replication (3SR) reaction in the in vitro amplification of nucleic acids", *Ann. Biol. Clin.*, 48 pp. 498–501 (1990).

Asseline, U., "Nucleic acid–binding molecules with high affinity and base sequence specificity:Intercalating agents covalently linked to oligodeoxynucleotides", *Proc. Natl. Acad. Sci. USA*, 81 pp. 3297–3301 (1984).

Asseline, U., "Oligodeoxynucleotides covalently linked to intercalating dyes as base sequence–specific ligands. Influence of dye attachment site" *EMBO Journal*, pp. 795–800 (1984).

Mariatis et al, Cold Spring Harbor Lab, 1982, Molecular Cloning, pp. 208 and 314.

Hames et al, Nucleic Acid Hybridization, 1985, IRL Press, p. 123.

Kwoh et al, Proc. Natl. Acad Sci, v. 86, Feb. 1989 p. 1173.
Guatelli et al, Proc. Natl Acad. Sci, v. 87, Mar. 1990, p. 1874.
Wu et al, Genomics, v. 4, 1989, p. 560.

*Primary Examiner*—Scott D. Priebe
*Attorney, Agent, or Firm*—Pillsbury Madison & Sutro, LLP Intellectual Property Group

[57] ABSTRACT

A homogeneous method for detecting amplified RNA or DNA target sequences utilizes signal-labelled DNA or RNA probes which show detectably increased fluorescence polarization when hybridized to target sequences. A convenient one-step analytical procedure requiring no nucleic acid extraction or signal separation step is thereby provided.

1 Claim, 8 Drawing Sheets

FIG. 1

```
2201  CAGCCCCACC AGAAGAGAGC TTCAGGTCTG GGGTAGAGAC AACAACTCCC
2251  CCTCAGAAGC AGGAGCCGAT AGACAAGGAA CTGTATCCTT TAACTTCCCT
2301  CAGATCACTC TTTGGCAACG ACCCCTCGTC ACAATAAAGA TAGGGGGGCA
2351  ACTAAAGGAA GCTCTATTAG ATACAGGAGC AGATGATACA GTATTAGAAG
2401  AAATGAGTTT GCCAGGAAGA TGGAAACCAA AAATGATAGG GGGAATTGGA
2451  GGTTTTATCA AAGTAAGACA GTATGATCAA ATACTCATAG AAATCTGTGG
2501  ACATAAAGCT ATAGGTACAG TATTAGTAGG ACCTACACCT GTCAACATAA
2551  TTGGAAGAAA TCTGTTGACT CAGATTGGTT GCACTTTAAA TTTTCCCATT
2601  AGCCCTATTG AGACTGTACC AGTAAAATTA AAGCCAGGAA TGGATGGCCC
2651  AAAAGTTAAA CAATGGCCAT TGACAGAAGA AAAAATAAAA GCATTAGTAG
2701  AAATTTGTAC AGAAATGGAA AAGGAAGGGA AAATTTCAAA AATTGGGCCT
2751  GAAAATCCAT ACAATACTCC AGTATTTGCC ATAAAGAAAA AAGACAGTAC
```

FIG. 2

HIV-DASH SEQUENCE

```
        |_____5' PRIMER_____|
        |                         |
        10        20        30        40        50
TTAGATACAG GAGCAGATGA TACAGTATTA GAAGAAATCA GTTTGCCAGG
AATCTATGTC CTCGTCTACT ATGTCATAAT CTTCTTTAGT CAAACGGTCC

DASH3
                    |_____(DASH3-AM1-FITC)_____|
                    |                                |
        60        70        80        90        100
AAGATGGAAA CCAAAAATGA TAGGGGGAAT TGGAGGTTTT ATCAAAGTAA
TTCTACCTTT GGTTTTTACT ATCCCCCTTA ACCTCCAAAA TAGTTTCATT

|_____ DASH1C _____|
                    |                        |
        110       120       130       140       150
GACAGTATGA TCAGATAGTC ATAGAAATCT GTGGACATAA ACCTATAGGT
CTGTCATACT AGTCTATCAG TATCTTTAGA CACCTGTATT TGGATATCCA 160       170       180       190       200
ACAGTATTAG TAGGACCTAC ACCTGTCAAC ATAATTGGAA GAAATCTGTT
TGTCATAATC ATCCTGGATG TGGACAGTTG TATTAACCTT CTTTAGACAA 210       220       230       240       250
GACTCAGATT GGTTGCACTTT AAATTTTCC CATTAGCCCT ATTGAGACTGT
CTGAGTCTAA CCAACCTGAAA TTTAAAAGG GTAATCGGGA TAACTCTGACA 260       270
ACCAGTAAAA TTAAAGCCAGG AATGGAT
TGGTCATTTT AATTTCGGTCC TTACCTA

____3' PRIMER_____|
                         |
```

```
FITC 5'                              3'
      G A T A G G G G G A A T T G G
              DASH3-15-AM1-FITC

DTAF 5'                              3'
      G A T A G G G G G A A T T G G
              DASH3-15-AM1-DTAF

3'                                                  5'
   G G T T T T T A C T A T C C C C C T T A A C C
                    T23-DASH1C
```

FIG. 7

```
DTAF 5'                              3'
      G A T A G G G G G A A T T G G
              DASH3-15-AM1-DTAF

3'                                                  5'
   G G T T T T T G C T A T C C C C C T T A A C C
                    T23-DASH1C-G

3'                                                  5'
   G G T T T T T A C T A T C C C C C T T A A C C
                    T23-DASH1C-A

3'                                                  5'
   G G T T T T T T C T A T C C C C C T T A A C C
                    T23-DASH1C-T

3'                                                  5'
   G G T T T T T C C T A T C C C C C T T A A C C
                    T23-DASH1C-C
```

FIG. 8

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (xi) SEQUENCE DESCRIPTION: SEQ ID NO:1:

```
CAGCCCCACC AGAAGAGAGC TTCAGGTCTG GGGTAGAGAC AACAACTCCC CCTCAGAAGC      60

AGGAGCCGAT AGACAAGGAA CTGTATCCTT TAACTTCCCT CAGATCACTC TTTGGCAACG     120

ACCCCTCGTC ACAATAAAGA TAGGGGGGCA ACTAAAGGAA GCTCTATTAG ATACAGGAGC     180

AGATGATACA GTATTAGAAG AAATGAGTTT GCCAGGAAGA TGGAAACCAA AAATGATAGG     240

GGGAATTGGA GGTTTTATCA AGTAAGACA GTATGATCAA ATACTCATAG AAATCTGTGG      300

ACATAAAGCT ATAGGTACAG TATTAGTAGG ACCTACACCT GTCAACATAA TTGGAAGAAA     360

TCTGTTGACT CAGATTGGTT GCACTTTAAA TTTTCCCATT AGCCCTATTG AGACTGTACC     420

AGTAAAATTA AAGCCAGGAA TGGATGGCCC AAAAGTTAAA CAATGGCCAT TGACAGAAGA     480

AAAAATAAAA GCATTAGTAG AAATTTGTAC AGAAATGGAA AAGGAAGGGA AAATTTCAAA     540

AATTGGGCCT GAAAATCCAT ACAATACTCC AGTATTTGCC ATAAAGAAAA AAGACAGTAC     600

(2) INFORMATION FOR SEQ ID NO:2:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (xi) SEQUENCE DESCRIPTION: SEQ ID NO:2:

TTAGATACAG GAGCAGATGA TACAGTATTA GAAGAAATCA GTTTGCCAGG AAGATGGAAA      60

CCAAAAATGA TAGGGGGAAT TGGAGGTTTT ATCAAAGTAA GACAGTATGA TCAGATAGTC     120

ATAGAAATCT GTGGACATAA ACCTATAGGT ACAGTATTAG TAGGACCTAC ACCTGTCAAC     180

ATAATTGGAA GAAATCTGTT GACTCAGATT GGTTGCACTT TAAATTTTCC CATTAGCCCT     240

ATTGAGACTG TACCAGTAAA ATTAAAGCCA GGAATGGAT                            279

(2) INFORMATION FOR SEQ ID NO:3:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (xi) SEQUENCE DESCRIPTION: SEQ ID NO:3:

ATCCATTCCT GGCTTTAATT TTACTGGTAC AGTCTCAATA GGGCTAATGG GAAAATTTAA      60

AGTGCAACCA ATCTGAGTCA ACAGATTTCT TCCAATTATG TTGACAGGTG TAGGTCCTAC     120

TAATACTGTA CCTATAGGTT TATGTCCACA GATTTCTATG ACTATCTGAT CATACTGTCT     180

TACTTTGATA AAACCTCCAA TTCCCCCTAT CATTTTTGGT TTCCATCTTC CTGGCAAACT     240

GATTTCTTCT AATACTGTAT CATCTGCTCC TGTATCTAA                            279

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

ACAGGAGCAG ATGATACAGT ATTAG                                            25

(2) INFORMATION FOR SEQ ID NO:5:

(i) SEQUENCE CHARACTERISTICS:
        (A) LENGTH: 26 base pairs
```

```
        (B) TYPE: nucleic acid
        (C) STRANDEDNESS: single
        (D) TOPOLOGY: linear (xi) SEQUENCE DESCRIPTION: SEQ ID NO:5:

CCTGGCTTTA ATTTTACTGG TACAGT                                              26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

GATAGGGGGA ATTGGAGGTT TTATCAAAGT                                          30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

ACTTTGATAA AACCTCCAAT TCCCCCTATC                                          30

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION:  Oligonucleotide is labeled with FITC (xi) SEQUENCE DESCRIPTION: SEQ ID NO:8:

GATAGGGGGA ATTGG                                                          15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION:  Oligonucleotide is labeled with APDTAF (xi) SEQUENCE DESCRIPTION: SEQ ID NO:9:

GATAGGGGGA ATTGG                                                          15

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

CCAATTCCCC CTATCATTTT TGG                                                 23
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

CCAATTCCCC CTATCGTTTT TGG        23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:12:

CCAATTCCCC CTATCTTTTT TGG        23

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

CCAATTCCCC CTATCCTTTT TGG        23

DETECTION OF DNA/RNA BY FLUORESCENCE POLARIZATION

This application is a continuation of application Ser. No. 07/683,923, filed on Apr. 11, 1991, now abandoned, which is a continuation-in-part of our prior application Ser. No. 7/430,844 filed Nov. 1, 1989, now abandoned.

FIELD OF THE INVENTION

The present invention relates to the field of detecting target nucleic acid sequences contained in complex biological mixtures. More particularly, the invention relates to detection of nucleic acid sequences originally present in such mixtures n extremely low concentrations, by first enzymatically amplifying the specific target sequences, and then detecting them in a substantially homogeneous assay utilizing fluorescence polarization. An increase in fluorescence polarization indicates the extent of hybridization of a probe with the amplified target sequences.

BACKGROUND OF THE INVENTION

In the study of cell populations associated with disease states it is frequently found that only a subpopulation of available susceptible cells actually exhibit the morbid phenotype. In infectious diseases, the proportions of cells which are passively or actively infected may be very low, and the disease caused by the infectious agent may go unnoticed clinically even though an infected individual can transmit the agent to others. Examples of such infectious agents are clammy, protozoans, certain bacteria, and many viruses.

Amongst viruses, the human immunodeficiency virus (HIV) is known to have an extremely long latent period before the onset of the clinical symptoms known as AIDS. Latency may extend to several years during which the infected individual is capable of transmitting the virus to others through intimate contact, sharing of intravenous injection apparatus, or through donation of blood products.

HIV infection is specific for thymus-derived lymphocytes (T cells), and in particular the subset T cells having immune helper function. These T cells possess highly specific HIV receptors on their surfaces to which the virus attaches to gain entry to the cell. Monoclonal antibodies, grouped generally in the CD4 cluster, see *Leukocyte Typing* III, Ed. A. J. McMichael, Oxford University Press, 1987, and specific for the HIV receptor, have been isolated heretofore (see Kung et al., U.S. Pat. No. 4,381,295). A signal molecule can be attached to such antibodies which binds selectively to those cells expressing the receptor antigen thereby identifying the helper T cell subpopulation. Quantitation of cell numbers of such lymphocyte subpopulations may conveniently be carried out in a flow cytometer.

In normal individuals approximately 50 percent of peripheral T cells are helper cells. In HIV infected patients, this proportion declines sharply because the virus is cytotoxic to helper T cells. In latent infections or early in the course of clinical disease, the proportion of the helper T cell population actually containing virus, in either lytic or latent phase, may be very low, even to the order of 1 to 1000. This means that in such patients, a 2 ml sample of blood may contain only one or a few copies of the virus or its genome. At his stage of infection, no antibodies to viral proteins can be detected, even with the most sensitive immunological techniques available. There is a great danger that individuals at such early stages of infection may transmit the virus in donated blood without the virus being detected by conventional screening methods.

The most sensitive immunological techniques are capable of detecting antibody by HIV at minimally 21 days post-infection. A variety of immunoassays for detection of HIV have been described including enzyme-linked immunoassays (ELISA), immunodiffusion assays, radioimmunoassays (RIA), and the classical Western blot. Also a number of distinct assay strategies have been developed. One group of assays utilizes HIV viral antigens, particularly viral protein containing epitopes in conserved domains, bound covalently to a solid matrix. The matrix-bound enzyme is contacted with a serum sample, and any anti-antigen antibodies contained therein bind to antigen. In the typical sandwich assay, antiserum raised in a heterologous species against human antibody antigens conjugated to an enzyme (ELISA), fluorescent molecule, or other signal generating substance, is then reacted with the washed matrix-bound antigen-antiantigen complex. The signal emitted by the signal generating substance is typically a chromophor, fluorescent signal, beta or gamma radiation, or other such measurable emission.

Alternatively, analysis of serum antibodies may be obtained by Western blot consisting of gel electrophoresis of viral proteins, electrotransfer of the proteins to blotting paper, followed by reaction with antisera, and color development of the individual protein bands. The Western blot analysis is employed on a confirming test by blood banks in blood screening procedures. For a general review of the various immunological methods available, see Stites et al., *Basic & Clinical Immunology*, Appleton & Lange, 1987.

There have been many attempts in the prior art to make detection of serum antibodies to HIV or other low concentration targets more sensitive and selective. The two major approaches have been target amplification and signal amplification. In signal amplification, the object is to couple a very low level signal event to a large number of subsequent secondary signals which can be detected and quantified. It is apparent that this coupling must be highly specific so that background secondary signals do not proportionally increase. One such signal amplification system takes advantage of the extremely high affinity of avidin for biotin. A large number of biotin molecules can be covalently coupled to an antibody specific for viral antigens. When reacted with fluorochome-coupled avidin a large complex is formed having unusually brilliant fluorescence. Another system utilizes a mixture of monoclonal antibodies conjugated to a signal generating substance, each individual antibody type being specific for a different structurally distinct epitope. The theory is that a greater number of signal generating antibody molecules will bind to antigen if there are no overlapping specificities.

Another approach is to target nucleic acid sequences of the virus with a homologous nucleic acid probe coupled to a signal amplification system. Under renaturing conditions the viral RNA (or denatured DNA) anneals to the complementary sequence of an oligonucleotide probe. Detection of the hybrid is afforded by signal generating substances covalently conjugated to the probe. Applicable to his approach are the enzyme proteolyzes a zymogen which then acts upon a substrate to generate a measurable signal. Many of the variations in such techniques are described in Lelie et al., *Detection of HIV Infection Using Second-Generation HIV Assay*, IV International AIDS Symposium, Stockholm, 1988.

The second major approach involves target amplification in which the target interacting with the signal-generating entity is itself multiplied in number. Since proteins cannot replicate, target amplification inherently requires a nucleic acid sequence, and an enzymatic system which can replicate the target sequence in vitro. One such target amplification technique is disclosed in U.S. Pat. No. 4,683,195 (Mullis et al.) and U.S. Pat. No. 4,683,202 (Mullis), and is called polymerase chain reaction (PCR) amplification.

In PCR, a mixture of nucleic acids containing a DNA sequence in a small quantity is heated to denature double stranded DNA. Primers consisting of a oligonucleotide capable of mediating DNA synthesis from a single stranded template is added under conditions which favor annealing of the primers to their specific complementary sequences. A thermostable DNA polymerase is added, and an extension reaction proceeds at 72° C. in the presence of deoxynucleotide triphosphates, adenosine triphosphate and cofactors. The reaction is run at high temperatures to avoid non-specific binding of primer to non-homologous sequences. Under these stringent conditions fidelity of polymerization to the desired sequences is very high.

After polymerization is complete, the mixture is again heated to denature the double stranded DNAs, and the extension reaction is repeated. Such repetition of extension polymerization may occur several times until the target sequence is amplified in numbers sufficient to detect by any of the signal-conjugated probe assays described hereinabove.

In a second target amplification scheme called TAS, a first primer oligonucleotide or oligonucleotide containing an RNA transcriptase promoter-binding sequence is annealed to the target sequence and extended by DNA polymerase or reverse transcriptase. Following melting, a second primer complementary to the newly formed oligomer in a region distal to the first primer binding sequence is added, annealed, and extended. The resultant duplex DNA oligomer thus has a sequence flanking the target region and containing a transcriptional promoter. Addition of RNA transcriptase, in the presence of oligonucleotide triphosphates, adenosine triphosphate, and cofactors institutes transcription in vitro yielding up to 1000 copies of the target sequence. The TAS methods have been disclosed in WO 88/01050 (Berg et al.).

In a variation of TAS, RNAse H is added to the reaction mix. RNAse H specifically catalyzes the step-wise hydrolysis of RNA bases in an RNA-DNA duplex, so that after a cDNA strand has been synthesized with reverse transcriptase the RNAse digests the RNA strand of the duplex to permit synthesis of the second complementary DNA strand by DNA polymerase. It will be apparent that since a heating step to melt the DNA-RNA duplex is unnecessary for cyclization of the reaction, the entire amplification can be performed in a single incubation. The disadvantages of the TAS and 3SR methods, compared to PCR is the lesser degree of stringency because of non-specific primer bonding at the lower temperature.

Finally, target amplification can be carried out in a ligase-mediated procedure. In this procedure, complementary primer sets form adjacent hybrids on both complementary strands of the target. Ligase then joins the primers together at the nick separation, after hybridization. The ligated double primer can then act as a template for further ligation of primers in a subsequent melting and rehybridization step.

After the target amplification, the nucleic acids are ordinarily extracted and the amplified sequences are detected by the procedures set forth hereinabove. It should be emphasized that the known procedures of the prior art are heterogeneous, that is, they require multiple steps in which the DNA is first hybridized to a signal generating probe, followed by a step in which the unhybridized probe is separated from hybridized probe. ordinarily different sets of reagents are required for signal generation than for probe hybridization and separation. A completely homogeneous method for detection of amplified nucleic acids without a separation step is unknown in the prior art.

SUMMARY OF THE INVENTION

In accordance with the present invention, nucleic acids amplified by any method are detected in a convenient homogeneous one-step method utilizing fluorescence polarization. The method of this invention comprises incubation of denatured amplified nucleic acids under hybridizing conditions with a nucleic acid probe of homologous sequence covalently coupled to a fluorophor. The fluorophor-conjugated probe is added at a concentration sufficient to produce a measurable increase in fluorescence polarization when hybridized to the amplified nucleic acid sequences, but not in an excess quantity so as to appreciable quench the increase in fluorescence polarization attributable to hybridization.

It will be apparent that the method of the present invention is adaptable to a simple automated format for convenient processing of a large number of samples. This is because there is no nucleic acid extraction step, and it is unnecessary to separate unhybridized probe from the mixture. Further, the increase in fluorescence polarization upon hybridization is virtually instantaneous, and no repetitious shifts in temperature are required in practicing the present method.

More particularly, the method of the invention comprises: a) Heating or otherwise denaturing a liquid mixture and for a length of time sufficient to separate duplex nucleic acids into single strands, b) adding a fluorochrome-conjugated nucleic acid probe having a base sequence complementary to a target sequence contained in the amplified nucleic mixture, c) lowering the temperature of the mixture for adjusting the pH to permit hybridization of probe sequences to amplified nucleic acids target sequences; d) incubating the mixture for a time sufficient for substantially complete hybridization to occur; and e) measuring the degree of fluorescence polarization.

In a preferred method, target nucleic acid sequences are incubated under hybridization conditions with a fluorescein-conjugated probe comprising an oligonucleotide having substantial complementarity to the target nucleic acid sequences, the fluorescein being amino-linked to the oligonucleotide probe through an aminochlorotriazinylaminoalkylphosphoryl group, incubating for a time sufficient to obtain substantially complete hybridization, and measuring the fluorescence polarization. Probes for detecting a target nucleic acid sequence are also disclosed which comprise a fluorescein-conjugated oligonucleotide sequence of substantial complementarity to the target nucleic acid sequence, the fluorescein molecule being amino-linked to the oligonucleotide portion through an aminochlorotriazinylaminoalkylphosphoryl group. Most preferred probes are selected from the group consisting of oligonucleotides substantially homologous to target nucleic acids containing a guanosine or cytosine base in the position immediately 5' of the base annealing to the fluorescein-labelled terminal nucleotide of the said probe.

A kit is also contemplated by this invention, comprising a vessel containing a concentrated buffer solution of a composition optimizing hybridization of nucleic acids but without interfering with the measurement of fluorescence polarization, and a second vessel containing a solution of one or a plurality of nucleic acid probes conjugated to one or a plurality of assays. The solutions of the kit of this invention are readily deliverable step-wise to a multiplicity of sample containers. The samples can be processed through each of the method steps without transferring to another container, so that the incubations and fluorescence polarization determination can be accomplished in the same vessel and same machine under automation.

BRIEF DESCRIPTION OF THE DRAWINGS

FIG. 1 is a nucleotide sequence (SEQ ID NO:1), showing the portion thereof that was utilized in the experiments of Example 1.

FIG. 2 gives the nucleotide sequences of SEQ ID NO:2 and SEQ ID NO:3. Probes that were utilized in some of the Examples are also shown (SEQ ID NO:4, SEQ ID NO:5, SEQ ID NO:6 and SEQ ID NO:7).

FIG. 7 is an illustration of 3 nucleic acid sequences utilized in assays in Example 5. These sequences are, from top to bottom, SEQ ID NO:8, SEQ ID NO:9 and SEQ ID NO:10, respectively.

FIG. 8 is an illustration of 5 nucleic acid sequence utilized in assays in Example 5. These sequences are, from top to bottom, SEQ ID NO:9, SEQ ID NO:11, SEQ ID NO:10, SEQ ID NO:12 and SEQ ID NO:13, respectively.

DETAILED DESCRIPTION OF THE PREFERRED EMBODIMENT

Figure 3:
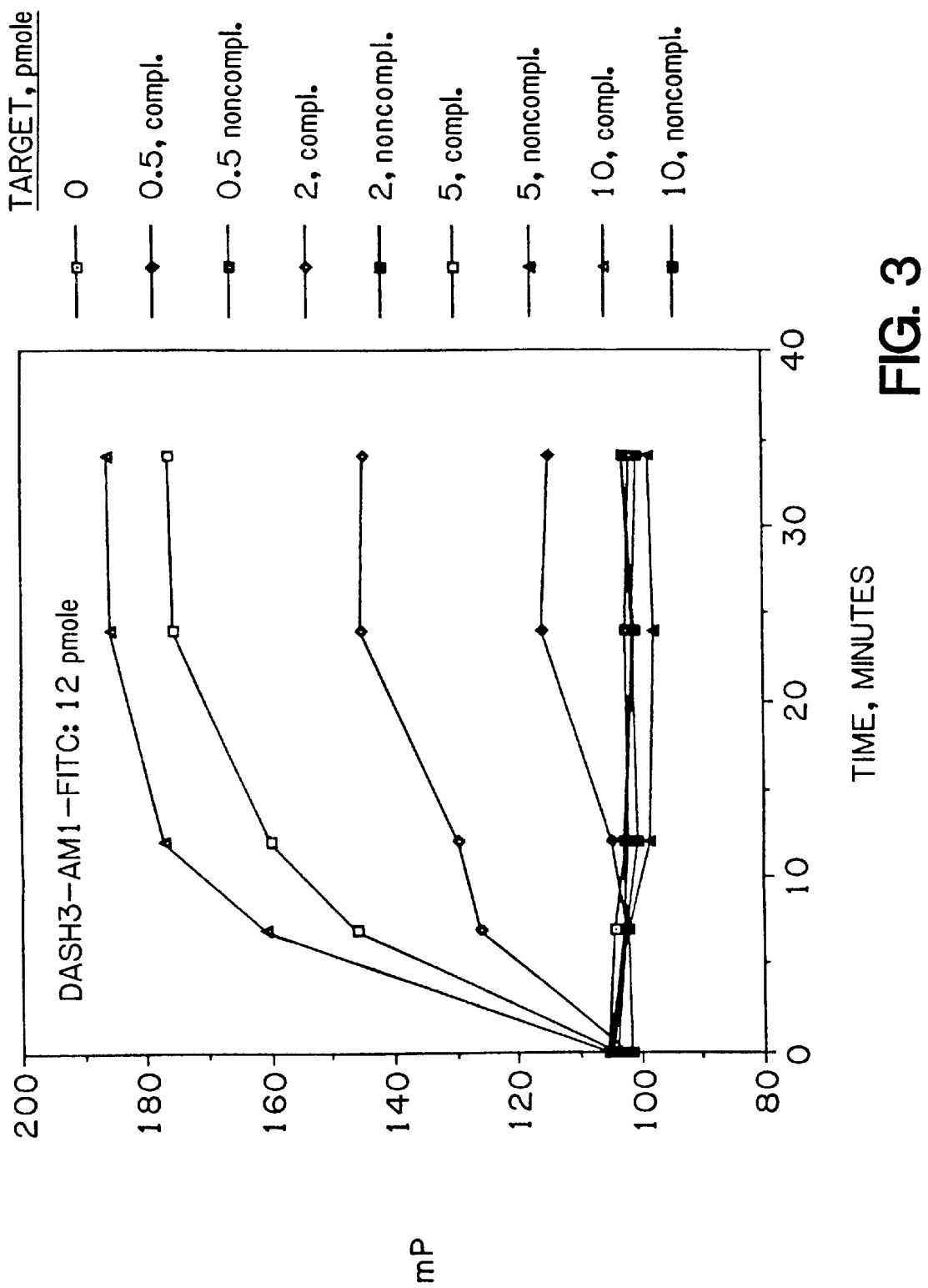
FIG. 3 is a rectilinear plot showing the fluorescence polarization data from Example 1.

In the technique of fluorescence polarization, light from a source is utilized to excite fluorescence emission from a fluorochrome molecule. A fluorophor or fluorochrome is a molecular entity, usually of molecular weight less than 10,000 daltons which emits fluorescent light at a characteristic wavelength when impacted with a radiant energy source. The fluorochrome is covalently coupled to a nucleic acid probe hybridizable with a complementary target amplified nucleic acid sequence. A variety of fluorochromes are known in the art which are adaptable to the present invention, including fluorescein derivatives, acidine orange (Van Bertalanffy et al., *J. Histochem. Cytochem.*, 4:481 (1956)), benzimidazole derivatives (Hilwig et al., *Exp. Cell Res.*, 75:122, 1972)), and a series of fluorescent nucleic acid stains, as disclosed in U.S. Pat. No. 4,544,546. In addition, oligonucleotides bonded to DNA intercalating agents have been utilized as nucleic acid probes, as disclosed in U.S. Pat. No. 4,835,263.

In the preferred embodiment, fluorescein is covalently attached to an oligonucleotide probe through an aminochlorotriazinylaminoalkyphosphoryl group having the generalized structure:

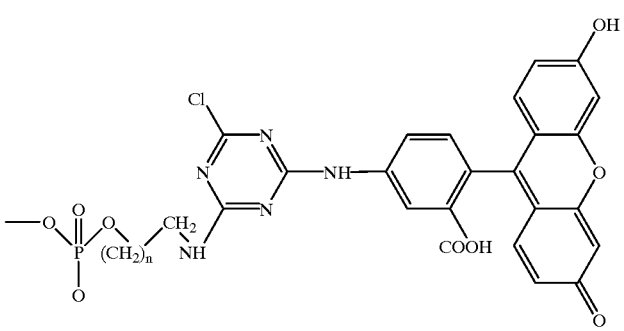

wherein n is an integer from 2 to about 12 (hereinafter referred to as APDTAF). Most preferred is the fluorescein conjugted oligonucleotide amino-linked through an aminochlorotriazinylaminoethylphosphoryl group. It has been determined empirically that compounds of the preferred generalized structure are superior in generating signal than other amino-linker configurations, such as carboxyfluorescein succinimidyl ester or the fluorescein isothiocyanate derivative (FITC) having the structure:

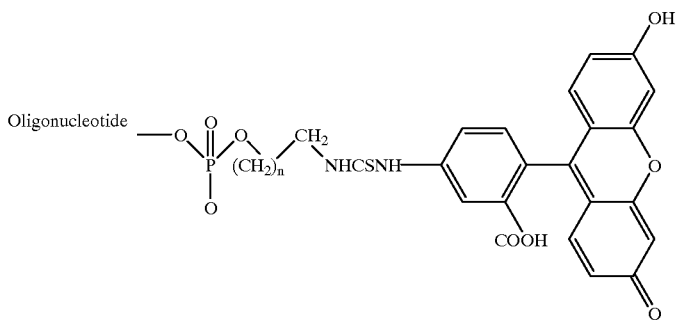

Applicants have further discovered that detection of hybridization by fluorescence polarization is substantially enhanced in the preferred APDTAF conjugated probe when the target sequence selected contains a guanosine or a cytosine base in the position immediately 5' of the base annealing to the fluorescein-labelled terminal nucleotide of the probe. The oligonucleotide portion of the probe has a sequence of substantial complementarity to the amplified target nucleic acids, so that a duplex between probe and target is formed. It is apparent that perfect complementarity is not necessary so long as a stable duplex is formed under the hybridization conditions utilized, and that some base mismatching may be tolerated. It is further apparent that these probes may be used in the detection of any substantially homologous target nucleic acid sequence, and is not limited to detection of only amplified nucleic acid.

The principle of this technique is based upon the characteristic rotational properties of molecules in solution. Molecules have a tendency to tumble about their various axes of rotation. In general, larger molecules tumble more slowly than smaller ones. Compared to the amplified DNA target molecules, the oligonucleotide fluorochrome-conjugated probes tumble very rapidly and along several axes of rotation. fluorescent light emitted from such spinning molecules is diffuse and characteristically multiplanar. However, when the probe molecule has annealed to the target sequence forming a substantially rigid structure of high molecular weight, it loses much of its spin. As a result fluorescence emission becomes relatively polarized. The emission fluorescence polarization of solution in which intercalating fluorochrome binds iwth DNA was described by Asseline et al., The EMBO J., 3, 795 (1984). This polarization effect can be measured conveniently in a fluorometer and a polarization value is calculated accordingly to the following equation:

$$P = \frac{I_{PA} - I_{PE}}{I_{PA} + I_{PE}}$$

wherein P is polarization units, $I_{PA}$ is the parallel intensity and $I_{PE}$ is the perpendicular intensity.

The oligonucleotide portions of the probe may have a variable number of bases, preferably about 10–40 which are substantially homologous with the target sequence. For generic identifications, it is important to select highly conserved regions of the genome so as to ensure substantial homology between different species, or genetic variants of the same infectious organism or other nucleic acid target. Further increased sensitivity of the present method may be attained by sue of more than one probe specific for different amplified sequences. In the case of HIV, selection of conserved sequences is an important consideration because the envelope proteins are genetically labile and mutant variations occur extremely rapidly. This has been found to result from replication errors. Reverse transcriptase is a highly imprecise replicator. On the other hand, since this property of the enzyme is particularly functional, the sequence encoding the enzyme itself is highly conserved. Accordingly, the sequences encoding the reverse transcriptase make excellent oligonucleotide probes which can be expected to hybridize to virtually any HIV variant. Conversely, selection of probes of short hybridizable sequences, preferable of 6 to 12 bases, from highly mutogeneic genomic regions may be utilized diagnostically to assess the degree of drift in homology over a period of time, or between different patient hosts.

As indicated hereinabove, there are now a number of different methods for amplifying nucleic acids. Once amplification has occurred, whether by PCR. TAS, 3SR, or LAS, the method of the present invention is equally applicable to detection of the nucleic acid so amplified, without regard to the amplification method used. It will be apparent to those skilled in the art that the inventive method of detection will be applicable as well to any future improvement or new technology in the nucleic acid amplification art.

The buffer utilized during hybridization may be selected from the group of buffers having buffering agents with a pH in the range of 6.5 to 8, having an ionic strength of 100 to 500 mM, and having 10 to 100 mM of a chelating substance. A typical buffer (20× concentration) is described in Maniatis et al., *Molecular Cloning*, 1982 and contains 200 mM sodium monobasic phosphate, 3 M sodium chloride, 20 mM ethylene diaminetetracetic acid, at pH 7.4 It was found empirically that this buffer provides good conditions for hybridization without appreciable quenching or other deleterious effect on the fluorescence polarization detection step.

The kit of the present invention provides a first vessel in which amplification of specific nucleic acid is done in a small volume. The amplified nucleic acid is then denatured by boiling or by the addition of sodium hydroxide. A second vessel of the kit contains the probe in a reconstitutable, lyophilized, or concentrated Liquid form which also contains hybridization buffer. The second vessel of the kit is made of a substance which does not readily absorb oligonucleotide molecules to its surfaces. Examples of such materials are polyethylene, polypropylene, teflon, silanized or siliconized glass. Finally, the opening of the vessels may have flange or valve means whereby to facilitate drawing of liquids contained therein into lines conveying the liquids to an automated machine for processing of a large number of amplified nucleic acid samples. Other advantages of the present invention will be apparent from the Examples which follow.

EXAMPLE 1

In initial experiments, the target sequence selected for study was a section of the HIVPV22 sequence partially encoding reverse transcriptase of HIV. A section of this sequence (bases 1195–2690) was cloned into plasmid p24L utilizing conventional techniques. The PCR reactions on both the plasmid and DNA from infected cells, termed HIV-DASH amplification region. The oligonucleotide primers, SEQ ID NO:4 and SEQ ID NO:5, at the 3' and 5' termini are shown on FIG. 2. Upon denaturation of HIV-DASH and annealing of the primers to their target sequences, DNA polymerase, preferably a highly purified form of recombinant enzyme from which the endonuclease encoding sequences have been deleted, is added to obtain chain extension. This procedure was repeated several times. This method of PCR amplification does not depart appreciably from the method disclosed in U.S. Pat. Nos. 4,683,145 and 4,683,202, and variations reported in the literature.

Upon completion of amplification, the nucleic acids are once again denatured. Denaturation can be effected thermally by boiling or, preferably, by addition of NaOH at 55° C. resulting in a pH of approximately 13. The fluorochrome-conjugated oligonucleotide probes are added. If denaturation was effected by boiling, renaturation will proceed by simply lowering the temperature to 37°–48° C. If denaturation was effected at high pH, then a sufficient amount of Tris pH 5.5 buffer is added to reduce the pH to 8, so that hybridization of probe proceeds.

Empirically, it was discovered that signal detection is enhanced when complementary probe pairs are employed, and also when more than one target sequence is used. Also, it was found that surprisingly a much better detection signal was generated in relatively large volumes of low target DNA concentration. Accordingly, the experiments of these examples were conducted in 1.5–2.0 ml volumes instead of 50 microliter microassays.

In the experiment of Example 1, reagents comprised a probe designated DASH3-AMI-FITC which has the oligonucleotide sequence described in SEQ ID NO:6 and shown in FIG. 2, covalently attached through an amide linkage to fluorescein isothiocyanate, a second unconjugated oligonucleotide sequence complementary to DASH 3-AMI-FITC (SEQ ID NO:6), designated DASHIC (SEQ ID NO:7), and a third unconjugated oligonucleotide sequence, designated DASH 3(SEQ ID NO: 6), as a noncomplementary control. These reagents were added together as follows: 1.9 ml 5× SSPE buffer (750 mM NaCl, 10 mM sodium phosphate monobasic, 1 mM EDTA); 100 microliters 120 nanomolar DASH3-AMI-FITC (SEQ ID NO:6) in 5× SSPE buffer, 5, 20, 50, 100 microliters respectively, in separate tubes, of 100 nanomaolar DASHIC (SEQ ID NO:7) in 5× SSPE buffer, or alternatively, 5, 20, 50, 100 microliters 100 nanomolar DASH3 (SEQ ID NO: 6) in 5× SSPE, respectively in separate tubes. Background fluorescence polarization values were obtained for each tube immediately after addition of the DASH3-AMI-FITC (SEQ ID NO:6) and before addition of the other oligonucleotides. After the hybridization reactions were begun, fluorescence polarization was monitored over a 35 minute period.

The results are shown in FIG. 3 of the drawings. It is readily apparent that hybridization of the fluorochrome-conjugated probe with its complementary probe sequence produces substantial polarization of fluorescence, and that the amount of polarization is substantially quantitative. This is essentially a control experiment demonstrating that hybridization to the relatively short complementary sequence brings about a significant degree of molecular spin inhibition.

EXAMPLE 2

Figure 4:
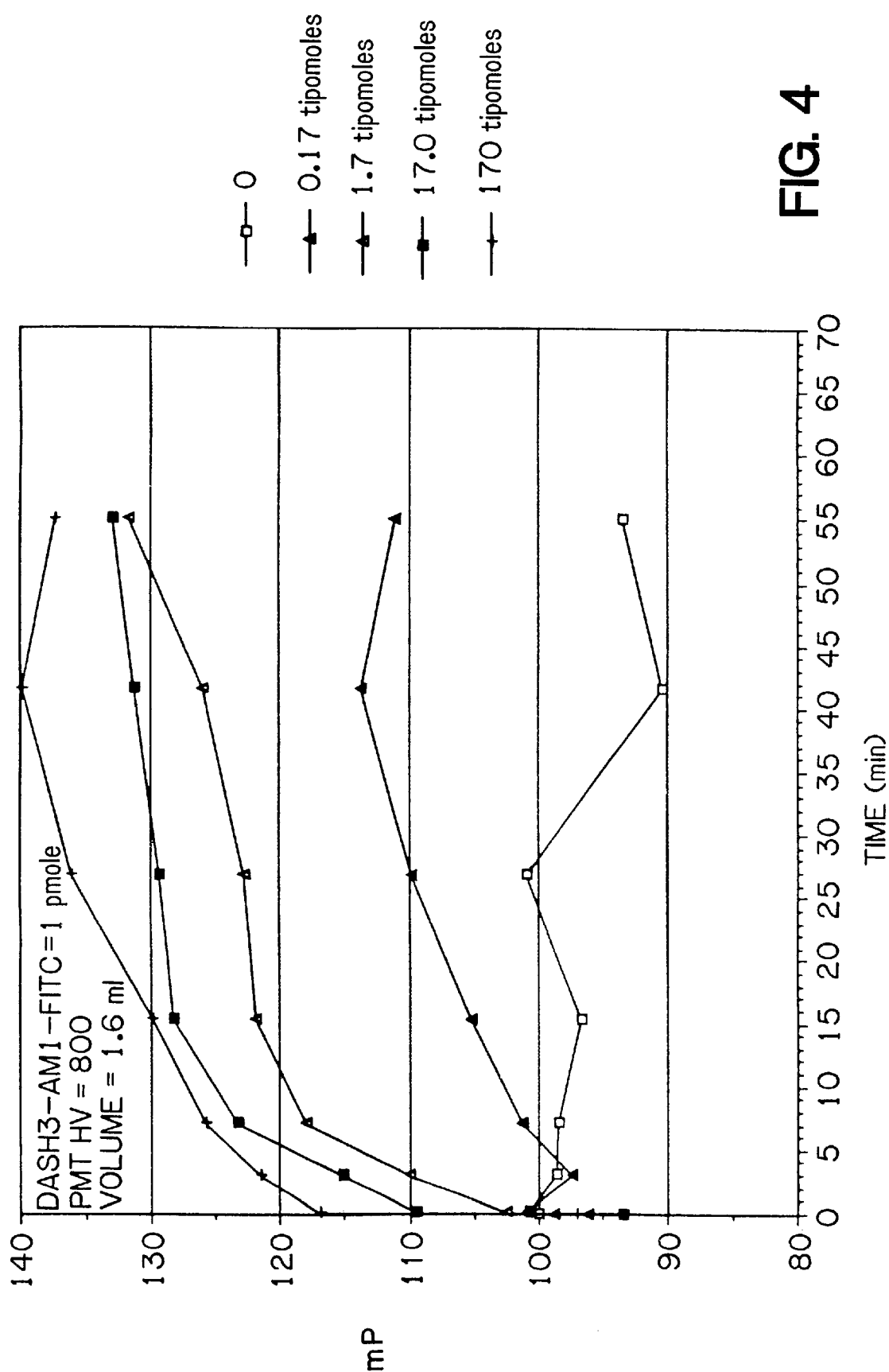
FIG. 4 is a rectilinear plot showing the detection of PCR amplified target by fluorescence polarization from Example 2.

In another experiment, of substantially identical format, the capture target sequence for labelled probe is a PCR amplified HIV target derived from amplification of the p24L plasmid known to contain the DASH sequence. The results are shown in FIG. 4 of the drawings. Hybridization was monitored over 55 minutes and carried out in a total reaction volume of 1.6 ml. The glossary of graph points on the right side of the figure expresses the DNA content of the reaction mix as the number of tipomoles of pre-PCR DNA present prior to the amplification step and, correspond to 0, $10^2$, $10^3$, $10^4$, and $10^5$ pre-amplification molecules of p24L plasmid DNA. Denaturation was carried out by incubating 20 microliters PCR reaction mix with 25 microliters water and 5 microliters NaOH at 55° C. for 15 minutes. Tubes containing 1.5 ml 5× SSPE buffer, 7 microliters of 3.2 M Tris-Hcl and 100 microliters DASH3-AMI-FITC (SEQ ID NO: 6) (10 mM in 5× SSPE buffer) were prepared and background fluorescence polarization measured. Fifty microliter aliquots of the PCR-DNAs were added and fluorescence polarization measured at the times indicated.

The results graphed in FIG. 4 of the drawings clearly show an increase in fluorescence polarization which is generally dose-dependent with increasing amounts of added PCR-DNA. This is an especially significant finding because of the large excess of DNA present which is noncomplementary to the DASH sequence in this homogeneous assay.

EXAMPLE 3

Figure 5:
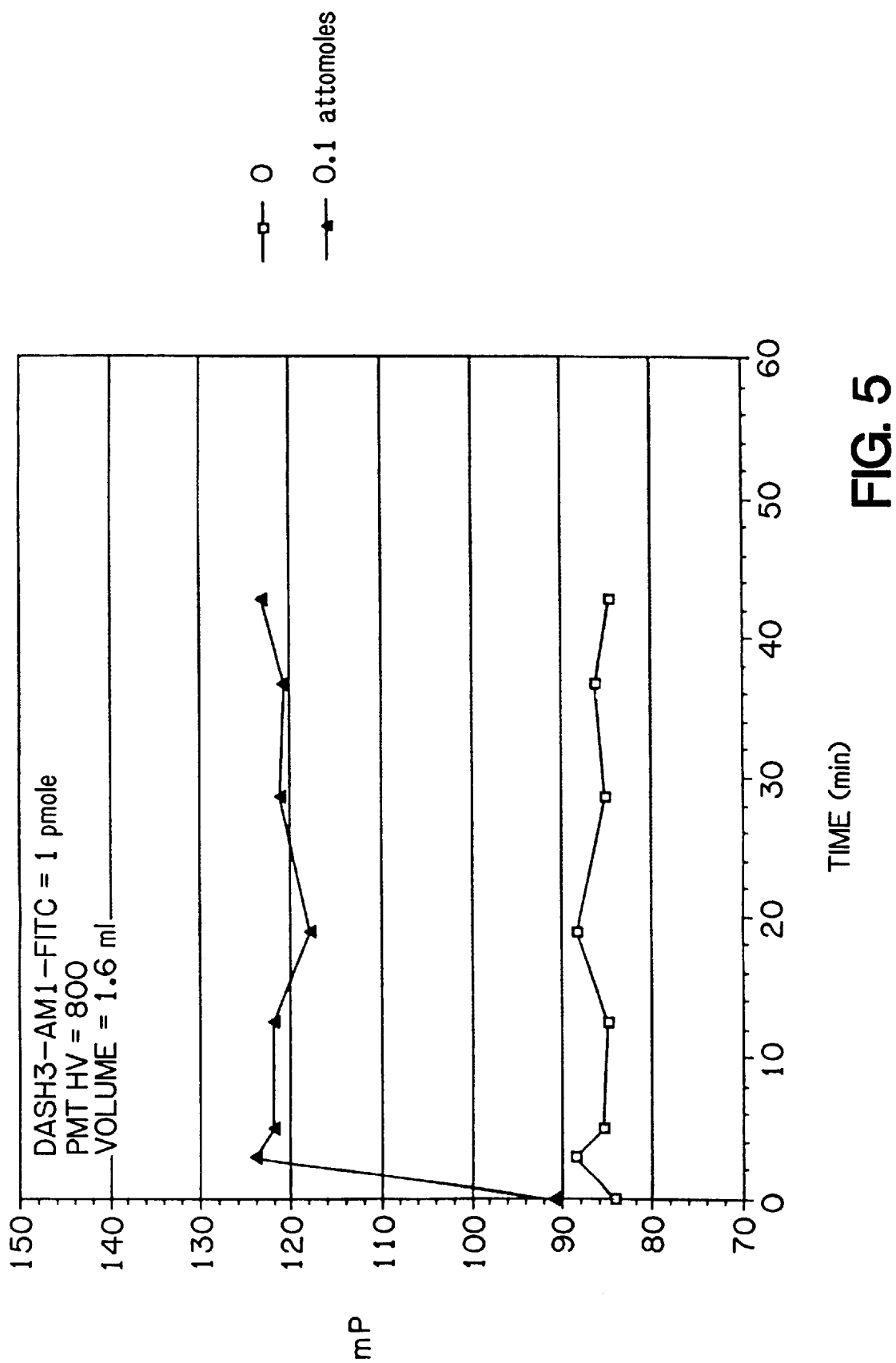
FIG. 5 is a rectilinear plot showing the detection of 3SR amplified target by fluorescence polarization from Example 3.

In a still further experiment the RNA fraction of H-9 cells infected with HIV virus was extracted by conventional methods. A portion containing 0.1 attomoles of HIV RNA was then amplified utilizing the 3SR amplification techniques described hereinabove. Test tubes for assay of probe-RNA hybrids were prepared by adding 1.5 ml 5× SSPE buffer to 100 microliters of a 10 mM DASH3-AMI-FITC (SEQ ID NO:6) solution. 3SR RNA was alkali denatured. Sixty microliters of the denatured 3SR amplified RNA was added to the test tubes, and fluorescence polarization was monitored over a 45 minute time period. The results, shown in FIG. 5, indicate that 3SR amplified RNA derived from the RNA fraction of HIV infected cells gives a strong, unequivocal positive signal compared to an unamplified control. This example illustrates that the detection method of the present invention is a versatile assay of nucleic acids containing target sequences amplified by any method.

EXAMPLE 4

Figure 6:
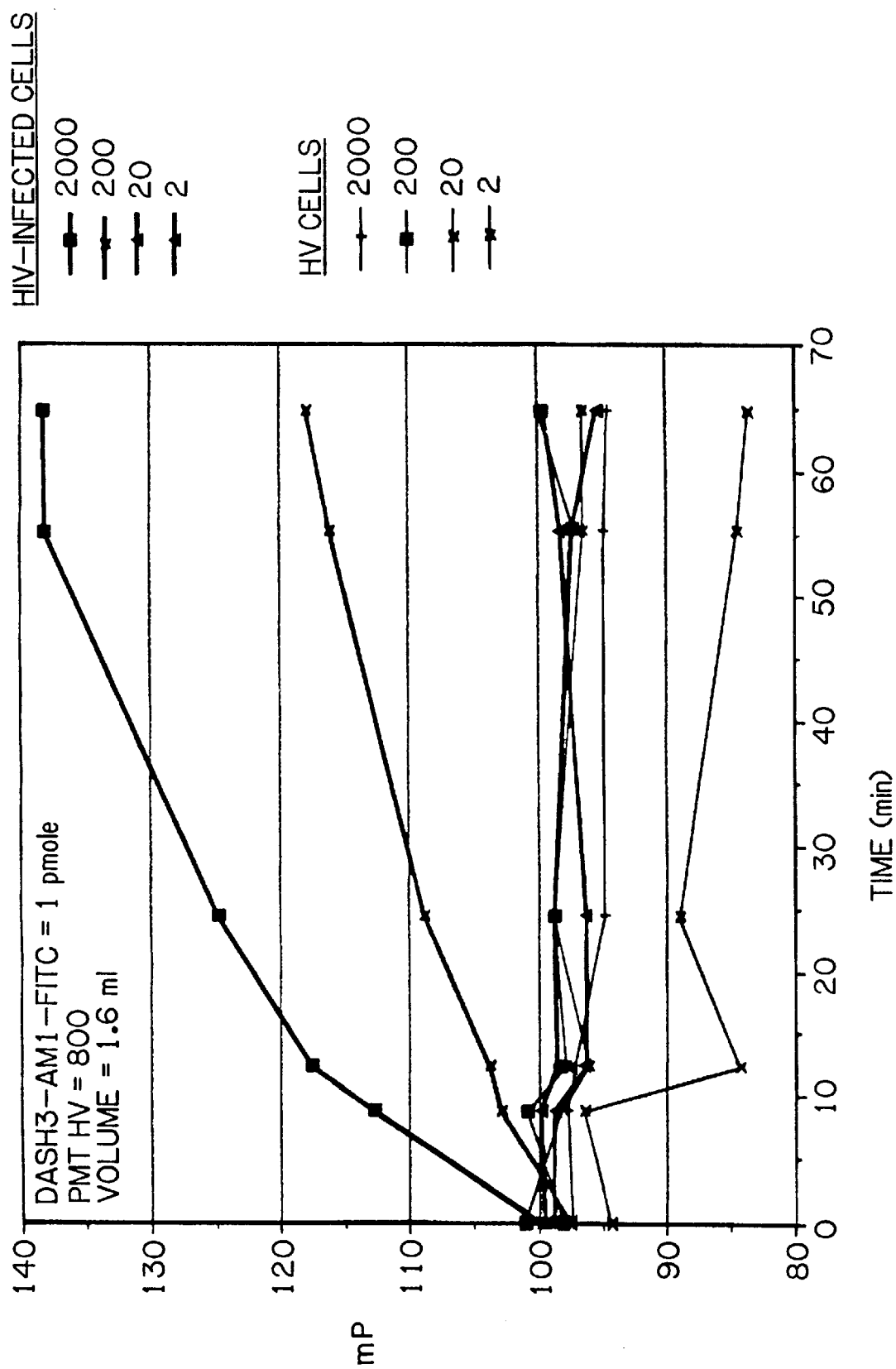
FIG. 6 is a rectilinear plot demonstrating the detection of target nucleic acids in HIV-infected H9 cells from Example 4.

In the experiment of this example, the resolving power of the present method was evaluated. The supernatant from a growing culture of H-9 cells infected with HIV was obtained and the DNA putatively contained therein was subjected to 60 cycles of PRC. The amounts of supernatant amplified corresponded to a volume of cultured cells containing $10^2$, $10^3$, $10^4$ cells. Similarly, identical control supernatants were prepared from growing cultures of non-infected H-9 cells. Test tubes were prepared containing 1.5 ml 5× SSPE buffer, 5 microliters 1N NaOH, 7 microliters 3.2 M Tris pH 5.5, and 100 microliters of 10 mM DASH3-AMI-FITC (SEQ ID NO:6). Target DNA was denatured by adding 5 microliters 1N NaOH and, 25 microliters water to 20 microliters PCR reaction mix followed by incubation at 55° C. for 15 minutes. Fifty microliters of the denatured PCR reaction solution was added to the test tubes containing the DASH3-AMI-FITC probe (SEQ ID NO:6) and hybridization proceeded with monitoring by fluorescence polarization. FIG. 6, shows that affirmative HIV sequence detection can be obtained of the PCR amplification of the supernatant containing as few as 200 cells. This means that the method of the present invention has sufficient sensitivity and resolving power to be useful as a routine serum screening assay for individuals with very early pre-clinical HIV infection.

In practicing the present invention, it must be emphasized that the probe technology and hybridization conditions are critical. The target sequences must have high binding affinity to probe and be highly specific for host sequences. Purity is also an important factor. Also, the fluorochrome-conjugated probe sequence length must be short enough that the rotational and relaxational properties show contrast in fluorescence polarization values when hybridized. Specific probe sequence may influence the rate at which annealing of probe to target sequence occurs, compared to the rate at which reannealing of native complementary target regions occurs. While is does appear that the amino-linker probe coupling strategy utilized in these examples is particularly efficacious, other linkage modes may theoretically be substituted by trial and error.

EXAMPLE 5

In these experiments the probe and target reagents were as follows: a probe designated DASH3-15-AMI-FITC which has the oligonucleotide sequence (SEQ ID NO:8) shown in FIG. 7 covalently attached through an amino-linker arm to fluorescein isothiocyanate, a second probe (SEQ ID NO:9) designated DASH3-15-AMI-APDTAF which has an identical sequence as the above probe but covalently attached through an amino-linker arm to dichlorotrianzinylaminofluorescein, and an unconjugated oligonucleotide target sequence (SEQ ID NO:10) designated T23-DASHIC which has the sequence shown in FIG. 7 and which is complementary to both of the above probes. In separate tubes each probe was added to the target sequence and fluorescence polarization was monitor as in Example 2. The results tabulated in Table 1 clearly shown that upon hybridization to a complementary target sequence, a probe labelled with APDTAF gives higher changes in fluorescence polarization (delta mP) than a probe labelled with FITC, upon hybridization to a complementary target sequence.

TABLE 1

| | FLUORESCENCE POLARIZATION (mP) | | |
| --- | --- | --- | --- |
| PROBE | Pre-hybridization | Post-hybridization | Delta |
| (SEQ ID NO:8) | 93.0 | 169.8 | 76.8 |
| (SEQ ID NO:9) | 111.8 | 240.1 | 128.3 |

Figure 9:
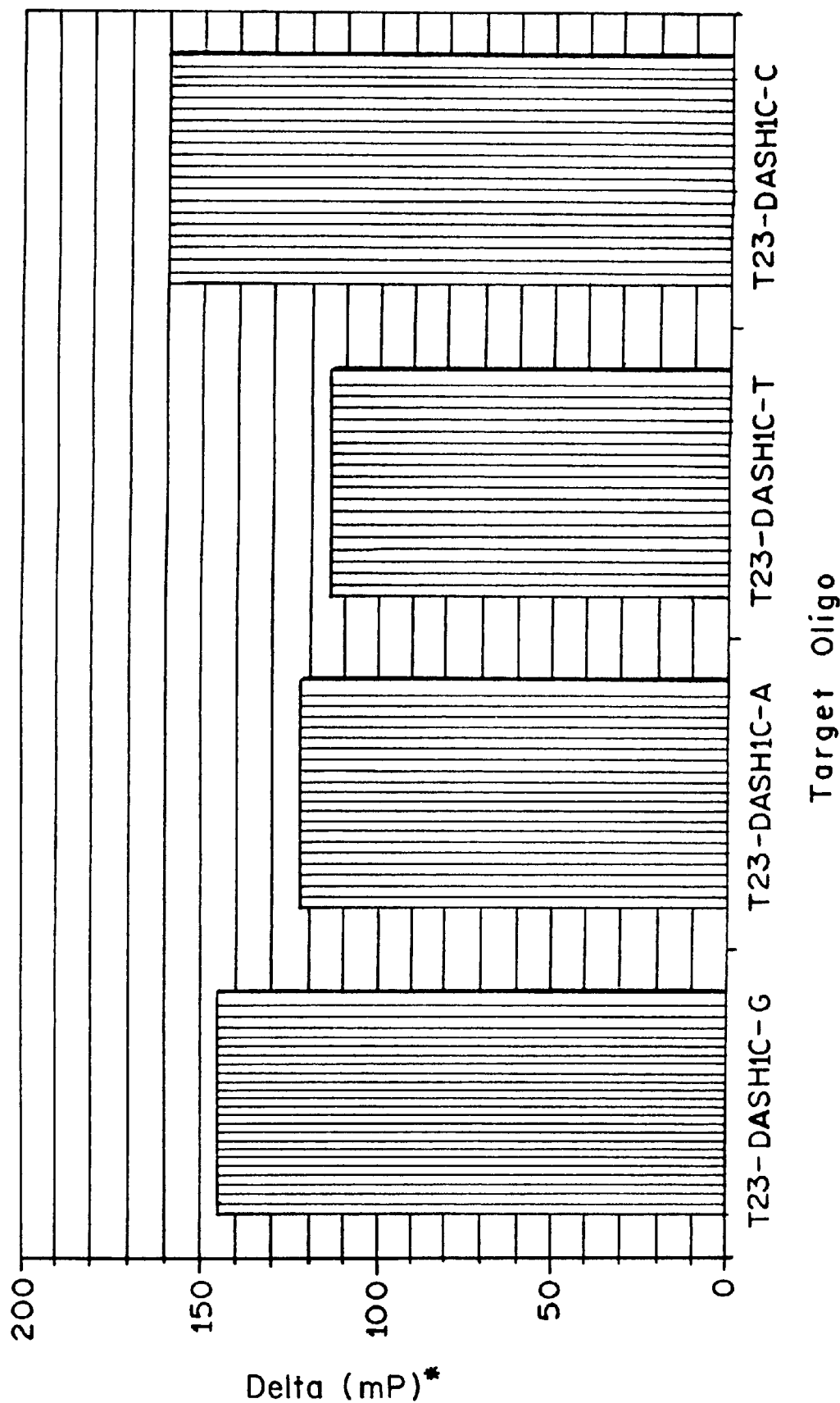
FIG. 9 is a bar graph illustrating the levels of fluorescence polarization obtained in Example 5 from 4 different probes.

In further experiments the probe and target were as follows: a probe (SEQ ID NO:9) designated DASH3-15-AMI-APDTAF which has the oligonucleotide sequence shown in FIG. 8 covalently attached through an amino-linker arm to dichlorotrianzinylaminofluorescein, and four unconjugated oligonucleotide target sequence designated T23-DASHIC-G, T23-DASHIC-A, T23-DASHIC-T, and T23-DASHIC-C which have the sequences (SEQ ID NO:11, SEQ ID NO:10, SEQ ID NO:12 and SEQ ID NO:13, respectively), shown in FIG. 8 and are complementary to the above probe. In separate tubes the probe was added to each of target sequences and fluorescence polarization was monitored as in Example 2. The results, graphed in FIG. 9 clearly, shows that the nucleotide of target sequence adjacent to the probes' linker arm after the hybridization affects the degree of fluorescence polarization. Greater changes (delta mP) in fluorescence polarization are obtained if the said nucleotide is a deoxycytidine (C) or a deoxyguanidine (G).

---

What is claimed is:

1. A method for detecting amplified target nucleic acid comprising the steps of:

(a) incubating single stranded, amplified nucleic acid suspected of containing said target nucleic acid with a fluorescein conjugated oligonucleotide probe having complementarity to said target nucleic acid, wherein said fluorescein is linked to said probe through an aminochlorotriazinylaminoalkyl-phosphoryl group;

(b) incubating for a time sufficient for hybridization of said oligonucleotide probe with said target nucleic acid to occur; and (c) detecting said target nucleic acid by measuring the degree of fluorescence polarization.

* * * * *